United States Patent [19]

Schmidt et al.

[11] Patent Number: 4,596,060
[45] Date of Patent: Jun. 24, 1986

[54] WORKTABLE

[75] Inventors: Helmut Schmidt; Anton Bodenmiller, both of Leutkirch; Alfred Straka, Isny, all of Fed. Rep. of Germany

[73] Assignee: Kaltenbach & Voigt GmbH & Co., Fed. Rep. of Germany

[21] Appl. No.: 634,980

[22] Filed: Jul. 27, 1984

[30] Foreign Application Priority Data

Aug. 10, 1983 [DE] Fed. Rep. of Germany ....... 3328919

[51] Int. Cl.$^4$ .............................................. A47L 5/38
[52] U.S. Cl. .................................... 15/312 R; 15/301; 15/314; 15/354; 55/DIG. 18; 98/115.4
[58] Field of Search ............ 15/301, 303, 310, 312 R, 15/312 A, 314, 345, 354; 55/385 R, 385 A, DIG. 18; 98/115 R, 115 LH, 115 SB, 115 VM

[56] References Cited

U.S. PATENT DOCUMENTS

| | | | |
|---|---|---|---|
| 3,292,525 | 12/1966 | Jenson | 55/DIG. 18 |
| 3,728,866 | 4/1973 | Layton | 55/DIG. 18 |
| 3,923,482 | 12/1975 | Knab | 55/DIG. 18 |
| 3,991,433 | 11/1976 | Cirino | 15/312 R |
| 3,994,042 | 11/1976 | Zakis | 15/312 R |
| 4,268,282 | 5/1981 | MacKenzie | 55/DIG. 18 |
| 4,490,881 | 1/1985 | Schmidt | 15/301 |

OTHER PUBLICATIONS

"Dust and Fume Control Equipment", Schmieg Industries, Nov. 16, 1965, p. 28.

Primary Examiner—Chris K. Moore
Attorney, Agent, or Firm—Scully, Scott, Murphy & Presser

[57] ABSTRACT

A worktable, in particular a dental laboratory workbench which includes a work block arranged at front side of the table, and a vacuuming device forming a unitary structure with the work block for vacuumable material or waste which is obtained during the processing or finishing of workpieces.

43 Claims, 14 Drawing Figures

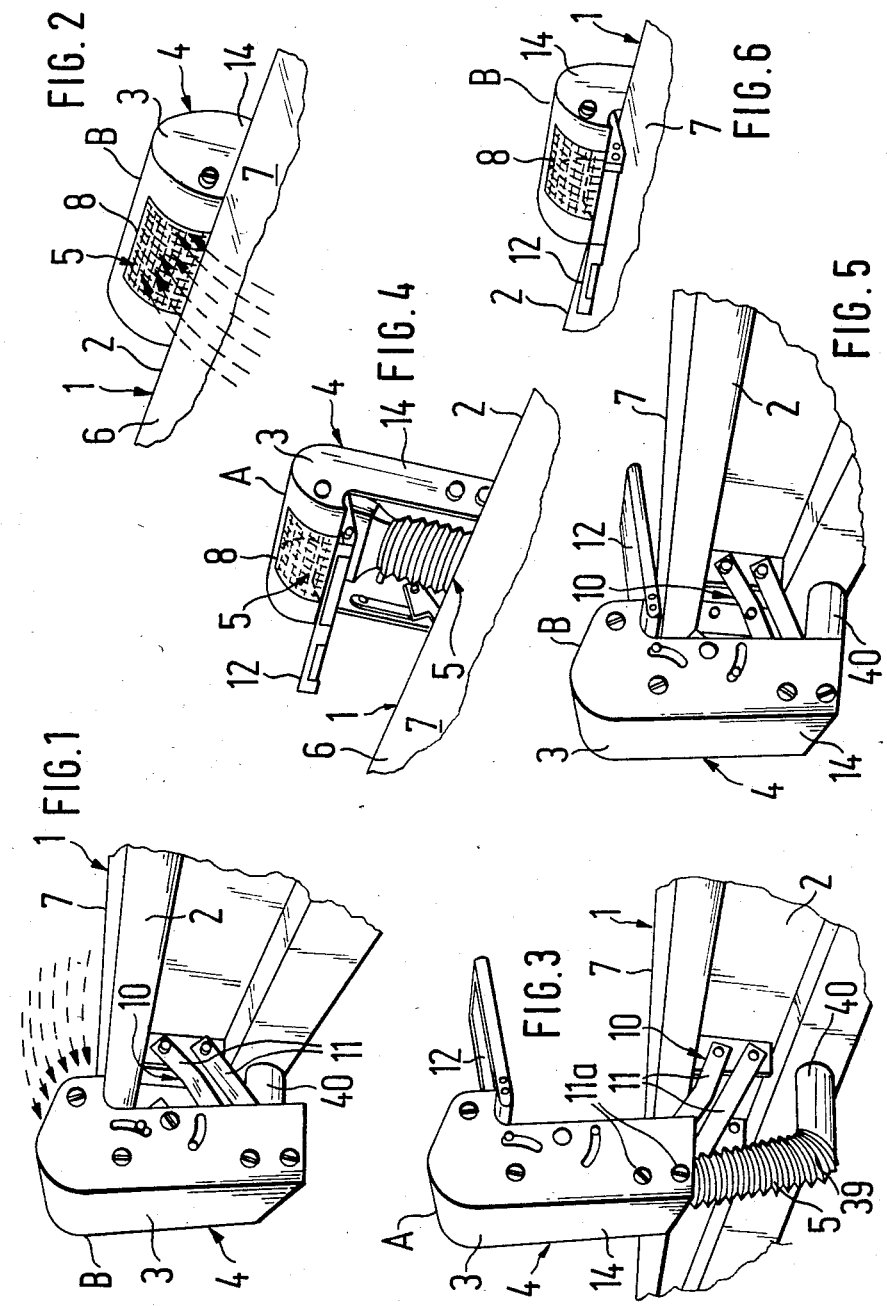

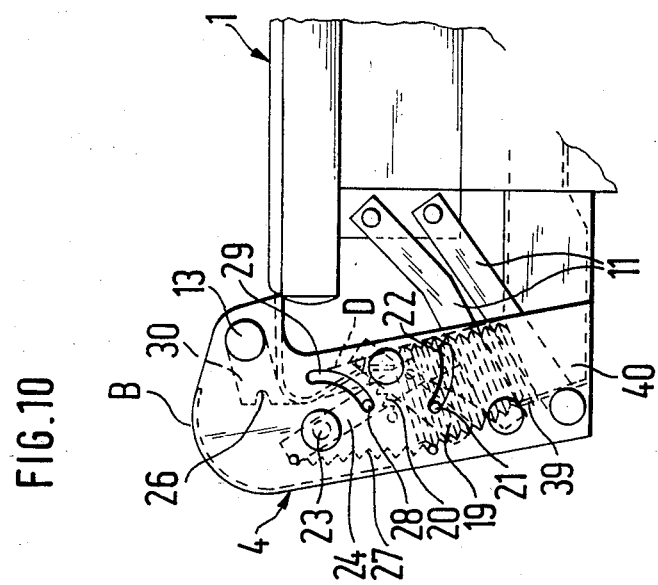
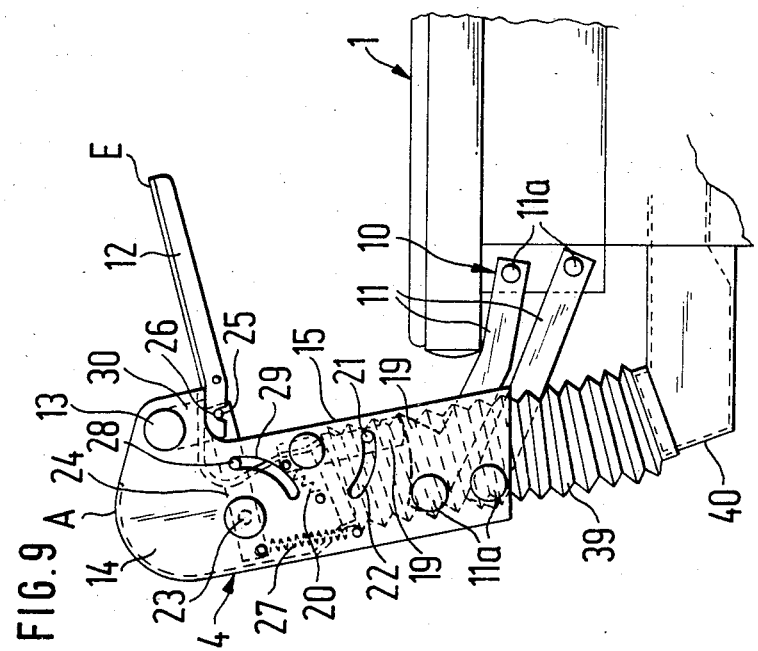

4,596,060

WORKTABLE

BACKGROUND OF THE INVENTION

1. Field of the Invention

The present invention relates to a worktable, in particular a dental laboratory workbench which includes a work block arranged at front side of the table, and a vacuuming device forming a unitary structure with the work block for vacuumable material or waste which is obtained during the processing or finishing of workpieces.

The vacuuming device serves for the suctioning of filings, polishing dust or other vacuumable material which is encountered in the area of the table plate, or of the work block which is also designated as a filing vice, particularly, as the result of the finishing of dental or dental technical workpieces.

A worktable of this type has become known from the disclosure of German Petty Patent No. 74 13 941. In this known prior art worktable, the vacuuming device incorporates vacuuming apertures which are only associated with the immovably positioned work block whereby, for the finishing of a workpiece which is carried out in the area of the table plate, there is not effected any or only a partial suctionable material vacuuming.

SUMMARY OF THE INVENTION

The present invention eliminates or ameliorates the above-mentioned disadvantages encountered in the prior art through the provision of a worktable of the above-mentioned type in which, during the finishing of workpieces in the are of the block as well as in the area of the table plate there is assured, in both instances an adequate and effective vacuuming of vacuumable waste material.

The advantages which are achieved through the present invention may be essentially ascertained in that every one of the working positions which are formed at different heights; for instance, even when the finishing or processing area is at a higher working position of the work block, as well as when the finishing area is in a lower working position of the table plate, will the suctionable waste material be vacuumed without encountering any problems.

BRIEF DESCRIPTION OF THE DRAWINGS

Advantageous modifications and features of the invention may now be ascertained the following detailed description of preferred exemplary embodiments thereof, invention, taken in conjunction with the accompanying drawings; in which:

FIG. 1 illustrates a perspective view of a vertically adjustable structural unit which is constituted of a work block and a vacuuming device arranged at the front side of a worktable, for example, a dental or dental laboratory workbench serving in a lower working position;

FIG. 2 illustrates a perspective view of the opposite side of the unit of FIG. 1;

FIG. 3 is a perspective view of the unit of FIG. 1 with a special work repository in a higher working location;

FIG. 4 is a perspective view of the unit of FIG. 3 from the opposite side thereof;

FIG. 5 is a perspective view of the unit of FIG. 3 in a lower working position;

FIG. 6 is a perspective view of the unit of FIG. 5 viewed from the opposite side thereof;

FIG. 9 is a side elevational view of the unit of FIG. 3, shown in part section and on an enlarged scale;

FIG. 10 is a side elevational view of the unit of FIG. 1, shown in part section and on an enlarged scale;

DETAILED DESCRIPTION

Figure 7:
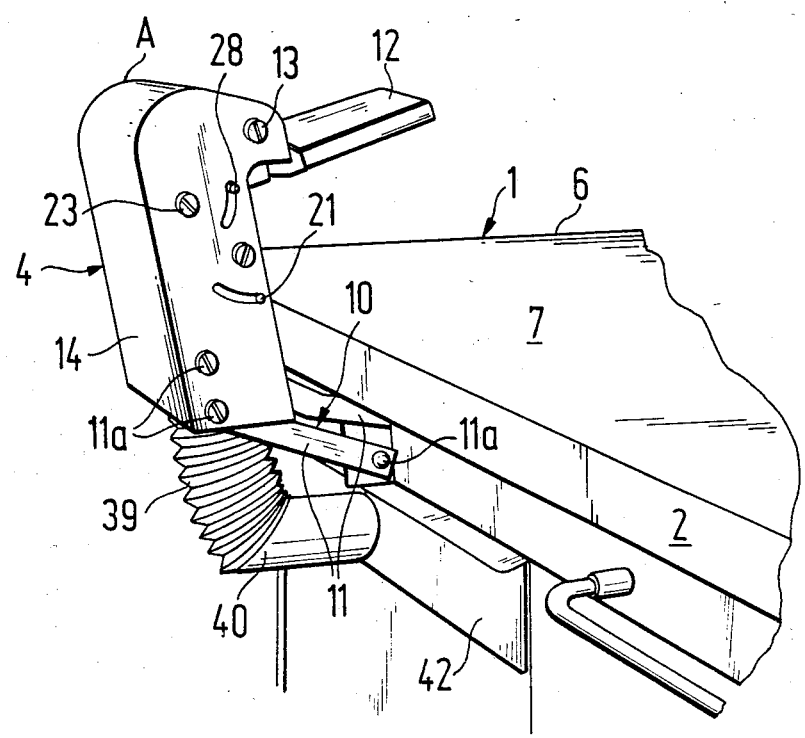
FIG. 7 is a perspective view of the unit of FIG. 3 with a vacuuming drawer, shown on an enlarged scale.
Figure 8:
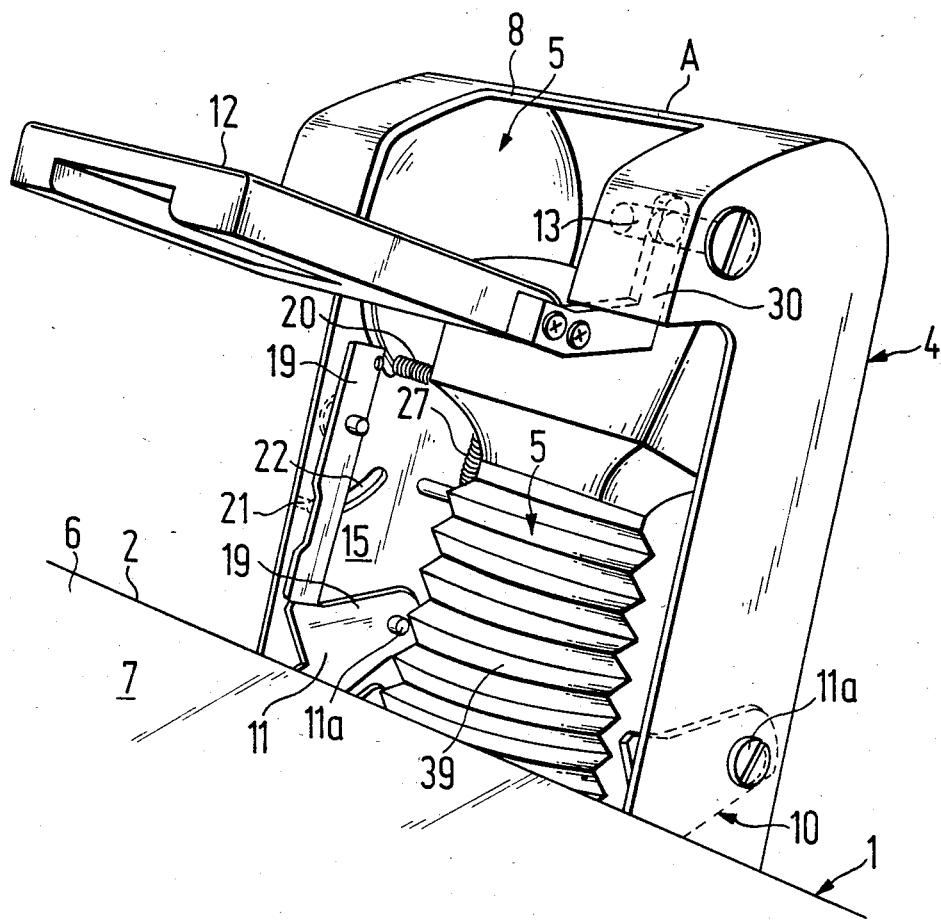
FIG. 8 is a perspective view of the unit of FIG. 4 shown on an enlarged scale.

The worktable 1 is provided at its front side 1 with a work block 3 and a vacuuming device 5 for suctionable waste material obtained during the finishing of workpieces, which device forms a structural unit 4 with the work block. The workblock-vacuuming device unit 4 is arranged on the table 1 so as to be adjustable in height to a plurality of positions A, B, A1; whereby the vacuuming device 5 includes at least one vacuuming opening 8; 8A, 8B of which at least one is operative in the work position A associated with the work block 3 as a finishing area in the region of the work block, and in another position 36 of the workblock 3 as work position A1 associated as a finishing area, or in a work position B associated with the table plate 6 as a finishing area in the region of the other position 36 or of the table top or plate 6.

From FIGS. 1 through 12 there can be ascertained that the oblong shaped unit 4 is movable from an upper work position A, which is associated with the work block 3 as a finishing area, into a lower work position B which is associated with the table top or plate 6 as a finishing or work processing area, whereby the suctioning opening 8 of the vacuuming device 5 of the unit 4 is located in both work position A, B above the surface 7 of the table plate 6 which, for the remainder, is also valid for any given set intermediate positions of the unit 4.

As can be ascertained, the suctioning opening 8 of the vacuuming device 5 is oriented in a direction extending away from a person seated ahead of the front side 2 of the table towards the table plate 6.

In accordance with FIGS. 11 and 12, the unit 4 is movable into a stored position C located below the surface 7 of the table plate 6, for which purposes there is provided in either the table plate, or as illustrated below the table plate 6, a storage niche 9 in the worktable 1 for the receipt of the unit 4 in the stored position thereof.

The unit 4 can basically be locked in all work positions A, B, A1 and/or also in the stored position C, and also in any given set intermediate positions between A and B or between B and C. A special embodiment with regard to the locking of the unit 4 in the upper work position A is detailed further on hereinbelow in connection with FIGS. 9 and 10. For effecting locking the of the unit there are provided special latching means.

In the embodiments pursuant to FIGS. 1 to 12, the unit 4 is connected with the table 1 through the intermediary of a parallelogram linkage arrangement 10, wherein the parallelogram linkage arrangement 10 consists of two parallelogram arms 11. The pivot points of the parallelogram arm 11 are identified by reference numerals 11a.

The unit 4 in the embodiments pursuant to FIGS. 1 through 12 is provided with a work repository 12 which, in the work positions A, B extends towards the suctioning opening 8, and which forms the work block 3 or a portion thereof, which forms the workpiece finishing area of the work block 3 and, additionally, can also serve as an intake guide for the vacuumable waste material into the vacuuming opening 8. For example, when the unit 4 is moved from the upper work position A into the lower work position B or into the stored position C, it is purposeful when, pursuant to FIGS. 9 and 10, the work repository 12 is movable into the unit 4 or, as illustrated, pivotable about a horizontal axis 13 into the unit 4. In the inoperative position B of the work repository 12 in which it pivoted into the unit 4, as well as in the work position E in which it is moved out of the unit, the work repository 12 can be locked in place with the aid of latching means, as is described in further detail hereinbelow.

The unit 4 consists of a housing 14 with a front side 15 which is open towards the table plate 6, and which is of such an opening height and width so that the working repository 12 is movable through the open front side into the housing.

Figure 12:
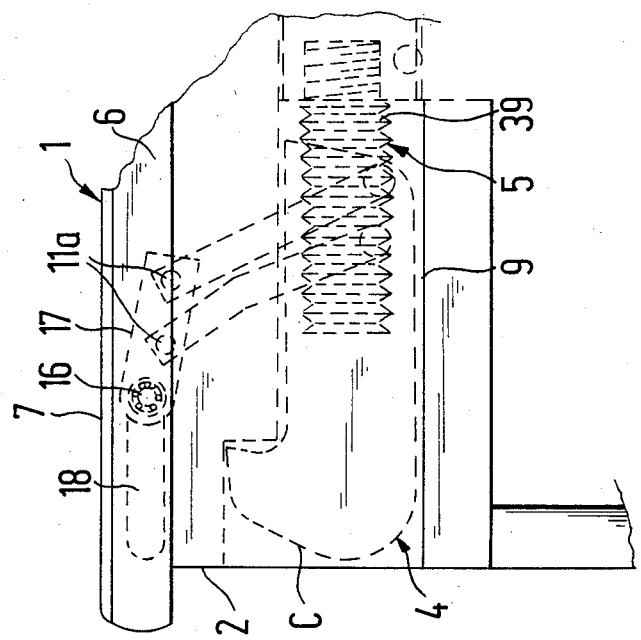
FIG. 12 illustrates the unit of FIG. 11 in a stored or inoperative position.
Figure 11:
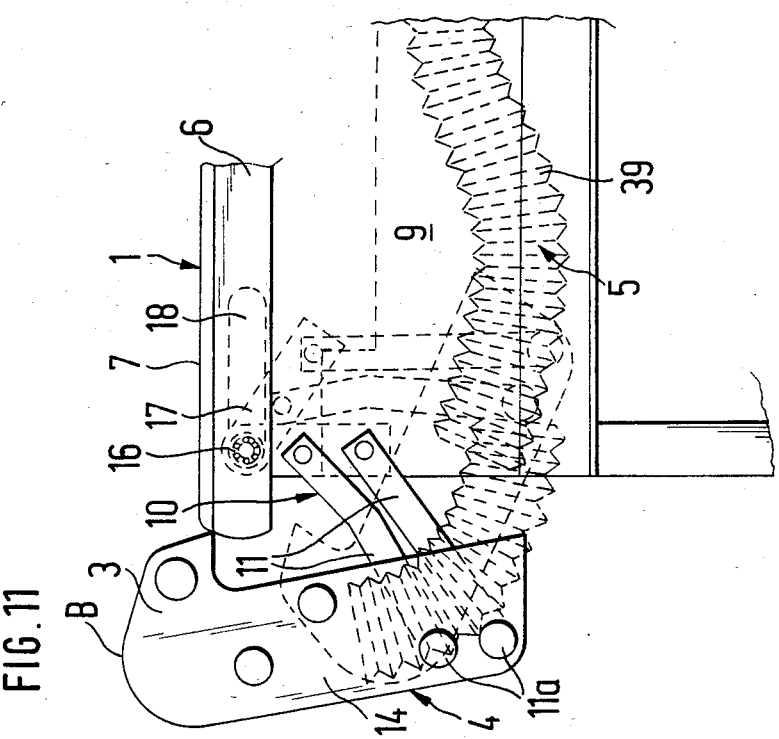
FIG. 11 illustrates the unit of FIG. 10 in a modified embodiment.

Especially, when in accordance with FIGS. 11 and 12, the unit 4 is movable into a stored position C, in order to provide for space-savings, it is purposeful when the ends of the parallelogram linkage arrangement 10 facing towards the table 1 are linked with a pivot lever 17 which, in the work position A, B of the unit 4, has it supper end supported so as to be pivotable about a horizontal axis 16 of the table 1, whereby the horizontal axis 16 and, consequently also the pivot lever 17, is supported so as to horizontally within elongated slots 18 in the table 1.

In accordance with FIGS. 9 and 10 the latching means which are provided for the locking of the unit 4 in the upper work position A, consists of a lever-like clamping element 19 which is movable from an inoperative position into a clamping position, and in the last-mentioned position will lock the parallelogram linkage arrangement 10 in its position relative to the unit 4; in effect will position and block. Thereby, the clamping element 19 is movable, in response to the action of a resetting element 20 which is constructed as a tension spring, into the clamping position which is associated with the upper work position A of the unit 4. In particular, for effecting the movement of the clamping element 19 into a non-clamping position in which the upper arm 11 of the parallelogram linkage arrangement 10 is released and which affords the movement of the unit 4 into the lower work position B, the clamping element 19 is provided with a handle 21 which is formed pin-like and which projects outwardly from the unit 4 through an arcuately extending slot 22 provided in one side wall of the housing 14.

As can be further ascertained, in particular from FIGS. 9 and 10, the latching means which are provided for the locking of the work repository 12 in the work position E in which it is pivoted out of the unit 4, incorporate a pivot lever 24 which is pivotable about a horizontal axis 23, which at its free end is provided with a pin-shaped engaging element 25 in the type of a sidewise projection for the locking and blocking engagement into a complementary engaging element 26 shaped as a type of detent for the work repository 12 in its work position E. Thereby, the pivot lever 24 has a resetting element 27 in the form of a tension spring associated therewith and which will retain it in the engaging position of its engaging element 26. For effecting the movement of its engaging element into the non-engaging position, the pivot lever 24 possess a handle 28 which is formed as a type of pin and projects outwardly from the unit 4 through a arcuately extending slot 29 which is provided in one side wall of the housing 14.

The work repository 12 has a shape of a bar which, at one end thereof, includes a bent portion 30 essentially upwardly pivoted at right angle in the work position E, and of which the free end is pivotable about the horizontal axis 13. Hereby, the complementary engaging element 26 is of the work repository 12 is located on the bottom side thereof at about the juncture with the bent portion 30.

Figure 13:
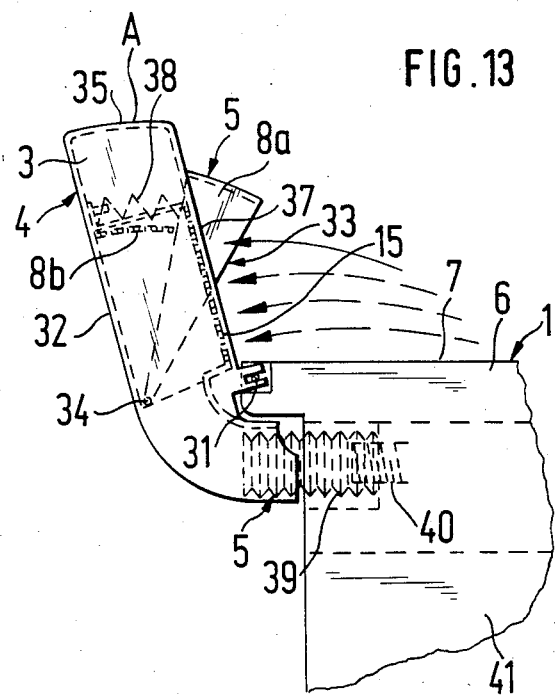
FIG. 13 illustrates a unit in a modified embodiment in a higher working position in a side elevational view and partly in section.
Figure 14:
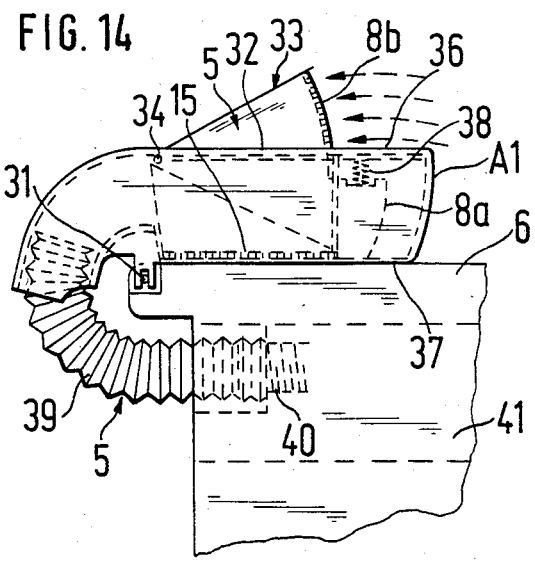
FIG. 14 illustrates the unit of FIG. 13 in a lower working position.

In the embodiment pursuant to FIGS. 13 and 14 the unit 4 is movable from a work position A which is associated with a direct finishing area above the work block 3 into a lower work position A1 associated with the work block 3 as a direct workpiece finishing area; however with another surface thereof, whereby the vacuuming device 5 evidences two suctioning openings 8A, 8B which are settable to, respectively, one of the two work positions A, A1. The unit 4, or the housing 14 thereof, has an oblong shape.

From FIGS. 13 and 14 there can be further ascertained that the unit 4 is pivotable about a horizontal axle 31 provided on the table 1 from the one into another of the work positions A or A1. The unit 4 can be locked in at least in one of the two work positions A or A1.

The unit 4 possesses a housing 14 with a front side 15 which opens towards the table plate 6, and with an oppositely located open rear side 32 whereby, in the housing 14 there is supported a vacuuming funnel 33 which incorporates the two suctioning openings 8A, 8B so as to be pivotable in such a manner about a horizontal axis 34, that in the upper work position A the one of the two suctioning openings on the front side 15 of the unit 4 will be operative in the lower work position A1 and the other of the two suctioning openings operative at the rear side 32 of the unit 4. The vacuuming funnel 33, for the assumption of its two end pivoting positions associated with the work positions A, A1 of the unit 4; is pivotable with the respective suctioning opening 8A or 8B from out of the front side 15 or, respectively, out of the rear side 32 of the unit.

FIGS. 13 and 14, further illustrate that the oblong shaped unit 4 in its upper work position A will essentially extend upwardly, whereby the upper side 35 of the unit forms the workpiece finishing area, whereas the unit 4 in its lower work position A1 extends beyond the table top or plate 6, and with the edge of the open front side 15 is located on the surface 7 of the table plate, wherein an unopened portion 36 of the rear side of the unit forms the finishing area. In order to intensify the vacuum effect of the suctioning opening 8B in the lower work position A1 of the unit 4, the edge of the open front side 15 is provided with a sealing lip 37 which extends complete about the opening and which comes into contact with the surface 7 of the table plate. Hereby, the vacuuming funnel 33, in response to the action of a resetting element 38 which is constructed as a coil tension spring, can be pivoted out with its one suctioning opening 8B from the open front side 15 of the unit 4. The unit 4 can be locked in the positions A and A1 and, when required, in any intermediate positions, for example, by means of locking means. In the same manner can the vacuuming funnel 33 be locked in its two positions, as can be ascertained from FIGS. 13 and 14.

In order to render easier the movement of the unit 4, the suctioning opening 8 or 8A, 8B of the vacuuming device 5 can be connected with a, for example, telescopically constructed vacuum conduit or hose. It is more suitable when, as illustrated in the drawing, the suctioning opening 8 or 8A, 8B of the vacuuming device 5 for the unit 4 is connected with a flexible vacuum conduit 39 which, in turn, is connected to a vacuum connector 40 on the table 1. Hereby, the vacuum hose conduit 39 is constructed in the type of a bellows.

The vacuum connector 40 is connected with a source of vacuum, in the illustrated case with a suction motor 41 which is arranged on the table 1.

In the embodiment according to FIG. 7, the vacuum connector 40 provided on a vacuum drawer 42 which is arranged in the table 1, which drawer, in turn, is provided with a suction motor.

The unit 4 can be detachably connected with the table 1; for example, by means of a socket plug connection.

What is claimed is:

1. In combination, a worktable with a work block arranged at the front side of the table, said work block having a vacuuming means arranged therein for removing vacuumable waste material from said work block or worktable during the finishing of work pieces, said combination comprising:
   (a) a work block being vertically adjustable on a worktable into a plurality of positions,
   (b) a vacuum means mounted within said work block including at least one suctioning opening, said means
   (c) operative in a first position associated with a finishing area of the work block,
   (d) and operative in a second work position associated with a table plate as a finishing area,
   (e) means for supporting said work block and vacuum means for pivotal movement through said plurality of positions, and into an inoperative and stored position.

2. A worktable as claimed in claim 1, wherein said first position is an upper work position using the work block as a finishing area, and the second position is a lower work position associated with the table plate as a workpiece finishing area, wherein the suctioning opening of said vauum means is in both work positions located above the surface of the table plate.

3. A worktable as claimed in claim 2, wherein said work block is lockable in intermediate positions between the lower work position and the stored position.

4. A worktable as claimed in claim 1, wherein said vacuum means includes a suctioning opening facing said table plate in a direction away from a person positioned in front of the table.

5. A worktable as claimed in claim 1, wherein said inoperative and stored position is arranged below the surface of the table plate.

6. A worktable as claimed in claim 5, wherein a storage niche is arranged in the table for receiving said unit in the stored position thereof.

7. A worktable as claimed in claim 5, wherein a storage niche is arranged below the table plate in said table for receiving said unit in the stored position thereof.

8. A worktable as claimed in claim 1, wherein the work block is lockable in at least one of said two work positions.

9. A worktable as claimed in claim 8, comprising latching means for locking the work block in position.

10. A worktable as claimed in claim 9, wherein said latching means for locking the work block in the upper work position comprises a clamping element which is movable from an inoperative position into a clamping position, and which in the clamping position locks the parallelogram linkage in position relative to said work block.

11. A worktable as claimed in claim 10, wherein the clamping element is movable into the clamping position responsive to the action of a resetting element.

12. A worktable as claimed in claim 10, wherein the clamping element includes a handle for effecting movement into a non-clamping position.

13. A worktable as claimed in claim 12, wherein said handle has a pin-like structure and projects outwardly from said work block through an arcuately shaped slot formed in a side wall of said housing.

14. A worktable as claimed in claim 1, wherein said work block is lockable in the stored position thereof.

15. A worktable as claimed in claim 1, wherein said work block is lockable in intermediate positions between said two work positions.

16. A worktable as claimed in claim 1, wherein said means for supporting said work block further comprises a parallelogram linkage for connecting said work block with the table.

17. A worktable as claimed in claim 16, wherein said parallelogram linkage comprises two parallelogram arms.

18. A worktable as claimed in claim 16, wherein the ends of the parallelogram linkage facing towards the table are linked with a pivot lever which is supported so as to be pivotably movable into the work positions, with the upper end of the work block pivoting about a horizontal axis of the table.

19. A worktable as claimed in claim 18, wherein the horizontal axis is supported for horizontal reciprocal movement in elongated slots formed in said table.

20. A worktable as claimed in claim 1, wherein the work block further includes a work repository extending in the work positions towards the suctioning opening, said repository forming at least a portion of said work block.

21. A worktable as claimed in claim 20, wherein said work repository is movable into said work block.

22. A worktable as claimed in claim 21, wherein said work repository is pivotable about a horizontal axis into the work block.

23. A worktable as claimed in claim 22, wherein said latching means for locking the work repository includes a pivot lever pivotable about a horizontal axis, said pivot lever herein equipped with an engaging element for locking engagement with a complementary engaging element of the work repository while in the work position.

24. A worktable as claimed in claim 23, wherein the pivot lever includes a resetting element restraining the lever in the engaging position of the engaging element.

25. A worktable as claimed in claim 23, wherein the pivot lever includes a handle for effecting movement into the non-engaged position of the engaging element.

26. A worktable as claimed in claim 25, wherein said handle has a pin-like structure and extends outwardly of the work block through an arcuately shaped slot formed in a side wall of said housing.

27. A worktable as claimed in claim 22, wherein the work repository has a bar configuration which, at one end, includes a bent portion essentially upwardly directed at right angles in the work position, the free end of said portion being pivotable about the horizontal axis.

28. A worktable as claimed in claim 27, wherein the complementary engaging element on the work repository is arranged on the lower side at the end of said bent portion.

29. A worktable as claimed in claim 21, wherein said work repository is lockable in an inoperative position within said unit and lockable in a work position extended outwardly from said work block.

30. A worktable as claimed in claim 29, which further includes latching means for locking said work repository in position.

31. A worktable as claimed in claim 21, wherein said work block further includes a housing having a front side open towards the table plate, said opening having a height and width to enable the work repository to move through the open front side into said housing.

32. A worktable as claimed in claim 31, wherein the work block housing has an oblong shapes.

33. A worktable as claimed in claim 1, wherein said work block is movable from a first work position wherein the upper end of the work block provides a direct workpiece finishing area into a second lower work position within the work block providing a second direct finishing area, said vacuum means including two suctioning openings adjustable to either one of the work positions.

34. A worktable as claimed in claim 33, wherein said work block is pivotable about a horizontal axis on the table from the first to the second work position.

35. A worktable as claimed in claim 33, wherein said work block is lockable in at least one of the two work positions.

36. A worktable as claimed in claim 33, wherein the work block includes a housing having a front side open towards the table plate and an oppositely-located open rear side, a vacuuming funnel which includes two suctioning openings, said funnel being supported so as to be pivotable about a horizontal axis in the housing, wherein in the first work position one of said two suctioning openings is operable at the front side of the work block and in the second work position the other of said two suctioning openings is operable at the rear side of the unit.

37. A worktable as claimed in claim 36, wherein the vacuuming funnel is pivotable to assume the two positions associated with the work positions of the work block, the respective suctioning opening being pivotable from the front side to the rear side of the work block.

38. Worktable as claimed in claim 36, wherein the oblong-shaped unit in the upper work position thereof extends thereof upwardly essentially upwardly in which the upper surface of the unit forms the finishing area, said unit in the lower work position thereof extending beyond the table plate and contacting with the edge of the open front side on the surface of the table plate whereby an unopened portion of the rear side of the unit forms the finishing area.

39. Worktable as claimed in claim 38, wherein the edge of the open front side is provided with a sealing lip extending about the opening and which is in contact with the surface of the table plate.

40. Worktable as claimed in claim 36, wherein the vacuuming funnel with one suctioning opening is pivotable outwardly from the open front side of the unit responsive to the action of the resetting element.

41. Worktable as claimed in claim 1, wherein the suctioning opening of the vacuuming means of the unit is connected to a flexible vacuum conduit which is connected to a vacuum connector on the table.

42. Worktable as claimed in claim 41, wherein the vacuum connector is connected with a suction motor.

43. Worktable as claimed in claim 41, in which the vacuum connector includes a vacuum drawer arranged in the table, and which is connected with a suction motor.

* * * * *